US 9,518,099 B1

(12) United States Patent
Liu

(10) Patent No.: US 9,518,099 B1
(45) Date of Patent: Dec. 13, 2016

(54) REFOLDED CHLOROTOXIN, CHLOROTOXIN VARIANT, REFOLDED CHLOROTOXIN VARIANT, AND PREPARATION TECHNOLOGY THEREOF

(71) Applicant: Wenzhou Institute of Biomaterials and Engineering, Wenzhou (CN)

(72) Inventor: Zhe Liu, Wenzhou (CN)

(73) Assignee: WENZHOU INSTITUTE OF BIOMATERIALS AND ENGINEERING, Wenzhou, Zhejiang (CN)

( * ) Notice: Subject to any disclaimer, the term of this patent is extended or adjusted under 35 U.S.C. 154(b) by 0 days.

(21) Appl. No.: 14/852,619

(22) Filed: Sep. 13, 2015

(51) Int. Cl.
*A61K 38/00* (2006.01)
*C07K 14/435* (2006.01)

(52) U.S. Cl.
CPC .............................. *C07K 14/43522* (2013.01)

(58) Field of Classification Search
None
See application file for complete search history.

(56) References Cited

U.S. PATENT DOCUMENTS

2012/0183544 A1* 7/2012 Sontheimer ...... A61K 47/48261
424/134.1

* cited by examiner

*Primary Examiner* — Thomas S Heard
(74) *Attorney, Agent, or Firm* — Leong C. Lei

(57) ABSTRACT

Disclosed are a folded chlorotoxin, a chlorotoxin variant and a folded chlorotoxin variant and their preparation technology. The folded chlorotoxin has a peptide sequence of MCMPCFTTDHQMARKCDDCCGGKGRGKCYGPQ-CLCR-NH$_2$, and the folded chlorotoxin variant has a peptide sequence of MCMPCFTTDHQMARSCDDCCGGSGRG-SCYGPQCLCR-NH$_2$ and is formed by replacing serine (Ser, S) by lysine (Lys, K) in the peptide sequence of chlorotoxin. The chlorotoxin and its derivatives have potential application values in biological and medical fields and good economic and social benefits to life, health, and personalized healthcare.

2 Claims, 8 Drawing Sheets

SEQUENCE LISTING

<160> NUMBER OF SEQ ID NOS: 2

<210> SEQ ID NO 1
<211> LENGTH: 36
<212> TYPE: PRT
<213> ORGANISM: leiurus quinque striatus

<400> SEQUENCE: 1

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 2
<211> LENGTH: 36
<212> TYPE: PRT
<213> ORGANISM: artificial sequence
<220> FEATURE:
<223> OTHER INFORMATION: synthetic

<400> SEQUENCE: 2

Met Cys Met Pro Cys Phe Thr Thr Asp His Gln Met Ala Arg Ser Cys
1               5                   10                  15

Asp Asp Cys Cys Gly Gly Ser Gly Arg Gly Ser Cys Tyr Gly Pro Gln
            20                  25                  30

Cys Leu Cys Arg
        35

REFOLDED CHLOROTOXIN, CHLOROTOXIN VARIANT, REFOLDED CHLOROTOXIN VARIANT, AND PREPARATION TECHNOLOGY THEREOF

TECHNICAL FIELD

The technical field relates to a folded chlorotoxin, a chlorotoxin variant, and a folded chlorotoxin variant, and their preparation technology.

BACKGROUND

In recent years, scholars discover that a polypeptide—chlorotoxin (CTX) with a segment composed of 36 amino-acid residues. The CTX has good tumor targetability capable of specifically combining different types of tumor cells such as giloma, sarcoma, colorectal, prostate cancers, etc. Researches show that CTX may be introduced into tumor cells through a matrix metalloproteinases-2 (MMP-2) medium, and MMP-2 is expressed in large quantity on the surface of tumor cells but not on the surface of normal cells. This explains why CTX specifically combines with tumor cells. Meanwhile, researches also show that CTX has a strong toxicity to invertebrates but no toxicity to mammals. At present, CTX modified radioactive treatment medicine 131I-TM-601 is adopted and filed for the approval by FDA and has entered into Phase II clinical trials. Some researches apply CTX and fluorescent dyes for displaying tumors in a surgical process. Therefore, CTX may become a targeting head group with high tumor specificity.

The current research trend aims at chlorotoxin, but the innovation on the folded structure and varied structure of chlorotoxin is poor, and thus restricting the potential of the application of chlorotoxin.

SUMMARY

In view of the present existing drawbacks and deficiencies of the prior art, it is a first objective of this disclosure to provide a folded chlorotoxin.

A second objective of this disclosure is to provide a preparation technology of the foregoing folded chlorotoxin.

A third objective of this disclosure is to provide a chlorotoxin variant.

A fourth objective of this disclosure is to provide a folded chlorotoxin variant.

A fifth objective of this disclosure is to provide a preparation technology of the foregoing folded chlorotoxin variant.

To achieve the aforementioned first objective, this disclosure provides a folded chlorotoxin with a peptide sequence of MCMPCFTTDHQMARKCDDCCGGKGRGKCYGPQ-CLCR-NH$_2$, and a structural formula of:

To achieve the aforementioned second objective, this disclosure provides a preparation technology comprising the steps of: creating a reacting system according to the following proportion of numeric values by weighing 40 mg of chlorotoxin, and putting the chlorotoxin in a container containing a mixed solution of 100 Mmol bicarbonate, 2~4 Mmol guanidine hydrochloride, 10~200 Mmol glutathione, and 10 wt % dimethylsulfoxide; and vortexing the reacting system until the solution becomes transparent and clear, and setting the reacting system in a refrigerating chamber at 4 degrees C. for a reaction of 1~24 hours to obtain a folded chlorotoxin product.

To achieve the aforementioned second objective, this disclosure provides a preparation technology comprising the steps of: creating a reacting system according to the following proportion of numeric values by weighing the chlorotoxin and putting the chlorotoxin in a container containing a mixed solution of 100 Mmol bicarbonate, 2 Mmol disodium edetate, 3 Mmol reduced glutathione, 1 Mmol oxidized glutathione, and having a pH-7.8, wherein the reacting system has a chlorotoxin concentration of 0.05 mg/ml; and vortexing the reacting system until the solution becomes transparent and clear, and setting the reacting system in a refrigerating chamber at 4 degrees C. for a reaction of 6 days to obtain a folded chlorotoxin product.

To achieve the aforementioned third object, this disclosure provides a chlorotoxin variant with a peptide sequence of MCMPCFTTDHQMARSCDDCCGGSGRGSCYGPQ-CLCR-NH$_2$ and formed by replacing serine (Ser, S) by lysine (Lys, K) in the peptide sequence of chlorotoxin and a structural formula of:

To achieve the aforementioned fourth objective, this disclosure provides a folded chlorotoxin variant with a peptide sequence of MCMPCFTTDHQMARSCDDCCGGSGRG-SCYGPQCLCR-NH₂; and formed by replacing serine (Ser, S) by lysine (Lys, K) in the peptide sequence of chlorotoxin, and a structural formula:

clear, and setting the reacting system in a refrigerating chamber at 4 degrees C. for a reaction of 6 days to obtain a folded chlorotoxin variant product.

The chlorotoxin variant and the folded chlorotoxin variant of this disclosure has potential application values in the biological and medical fields, and the chlorotoxin variant To achieve the aforementioned fifth objective, this disclosure provides a preparation technology comprising the steps of: creating a reacting system according to the following proportion of numeric values by weighing 38 mg of chlorotoxin variant, and putting the chlorotoxin variant into a container containing a mixed solution of 100 Mmol bicarbonate, 2~4 Mmol guanidine hydrochloride, 10~200 Mmol glutathione, and 10 wt % dimethylsulfoxide; and vortexing the reacting system until the solution becomes transparent and clear, and setting the reacting system in a refrigerating chamber at 4 degrees C. for a reaction of 1~24 hours to obtain a folded chlorotoxin variant product.

To achieve the aforementioned fifth objective, this disclosure further provides a preparation technology comprising the steps of: creating a reacting system according to the following proportion of numeric values by weighing a chlorotoxin variant and putting the chlorotoxin variant into a container containing a mixed solution of 100 Mmol bicarbonate, 2 Mmol disodium edetate, 3 Mmol reduced glutathione, 1 Mmol oxidized glutathione, and having a pH-7.8, wherein the chlorotoxin variant in the reacting system has a concentration of 0.05 mg/ml, and vortexing the reacting system until the solution becomes transparent and and the folded chlorotoxin variant are expected to be applied extensively in the areas of selectively binding cancer cells to targeting cancer diagnosis and treatment, marking and tracking of in vivo molecular probe, drug metabolism, screening, and optimization, and improving the targeting slow release of medicine and the accuracy of cancer surgery to provide excellent economic and social benefits to life, health and personalized healthcare.

In addition, the synthesis technology of this disclosure requires mild conditions and simple and easy separation and purification techniques and features the easy implementation of automated control and eco-friendliness.

DESCRIPTION OF THE PREFERRED EMBODIMENTS

This disclosure will become clearer in light of the following detailed description of an illustrative embodiment of this invention described in connection with the drawings. It is intended that the embodiments and drawings disclosed herein are to be considered illustrative rather than restrictive.

Refer to FIGS. 1 to 8 for the following embodiments of this disclosure.

Embodiment 1

Figure 1:
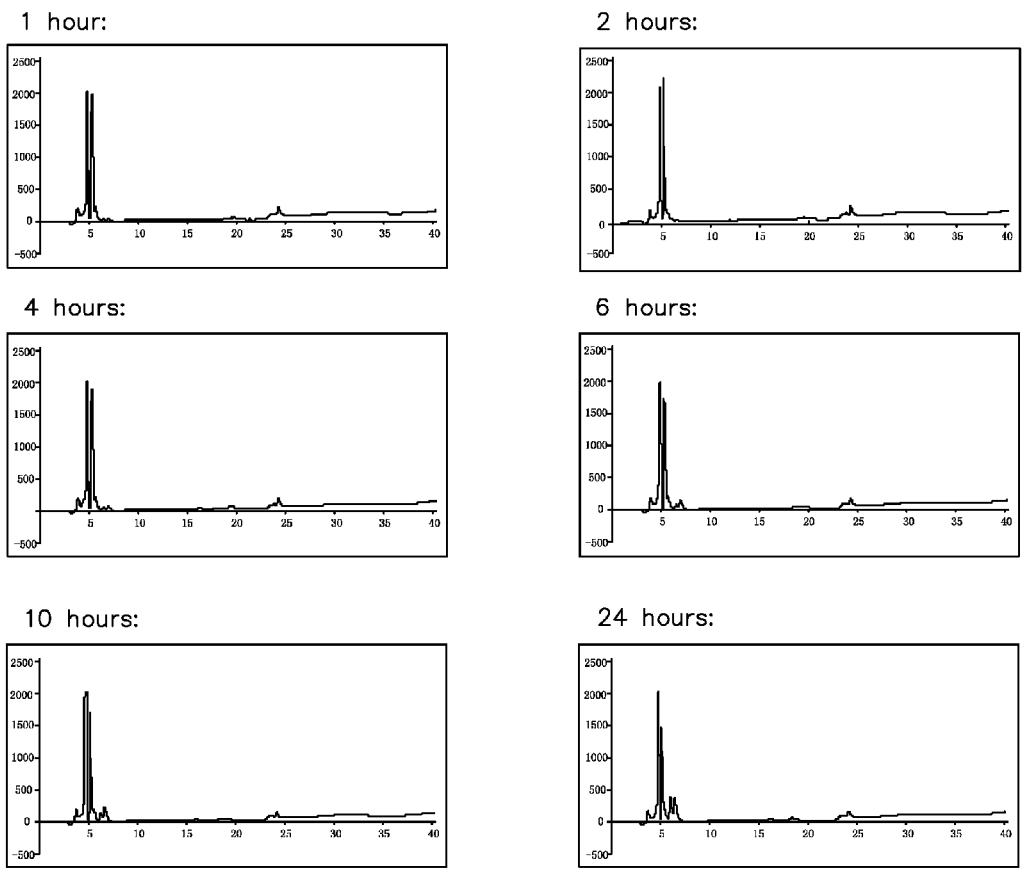
FIG. 1 shows the spectrum of a high performance liquid chromatography separation of folding reactions of chlorotoxin in different conditions in accordance with a first preferred embodiment of this disclosure.
Figure 2:
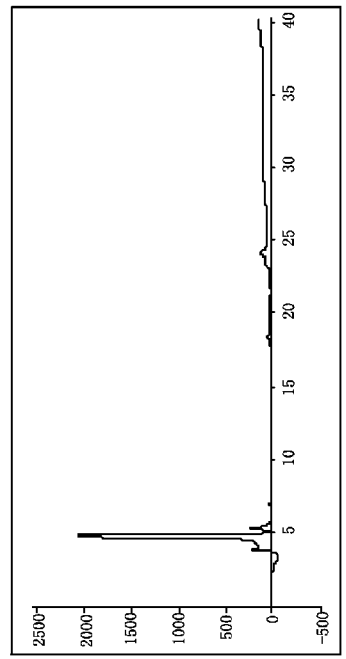
FIG. 2 shows the spectrum of a high performance liquid chromatography separation of folding reactions of chlorotoxin in different conditions in accordance with a second preferred embodiment of this disclosure.
Figure 2:
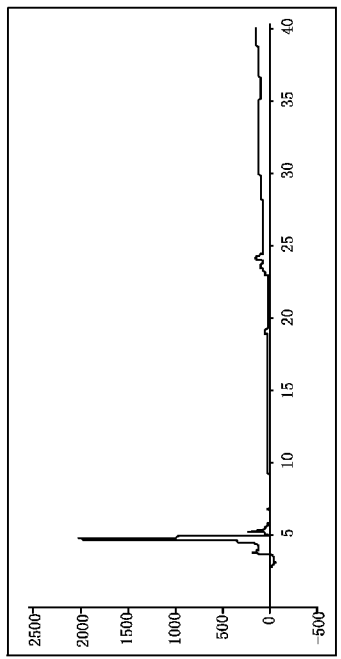
Figure 2:
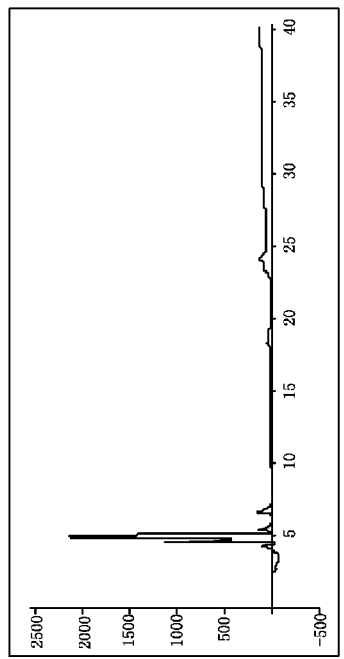
Figure 3:
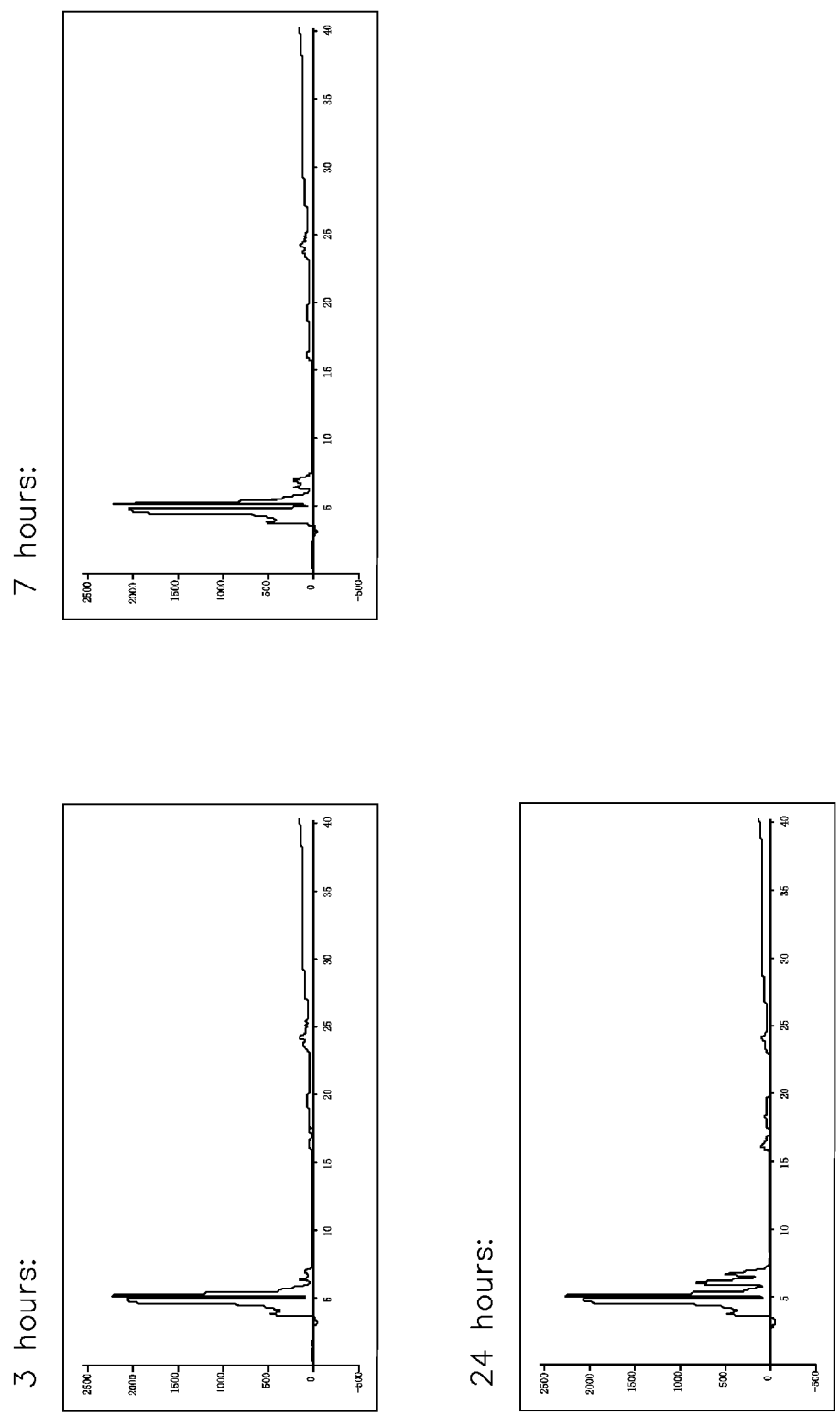
FIG. 3 shows the spectrum of a high performance liquid chromatography separation of folding reactions of chlorotoxin in different conditions in accordance with a third preferred embodiment of this disclosure.
Figure 4:
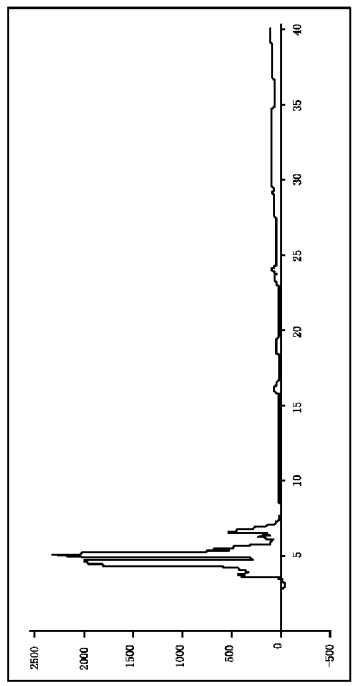
FIG. 4 shows the spectrum of a high performance liquid chromatography separation of folding reactions of chlorotoxin in different conditions in accordance with a fourth preferred embodiment of this disclosure.
Figure 4:
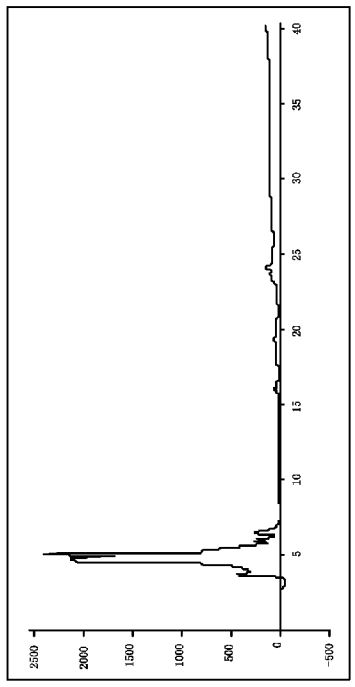
Figure 5:
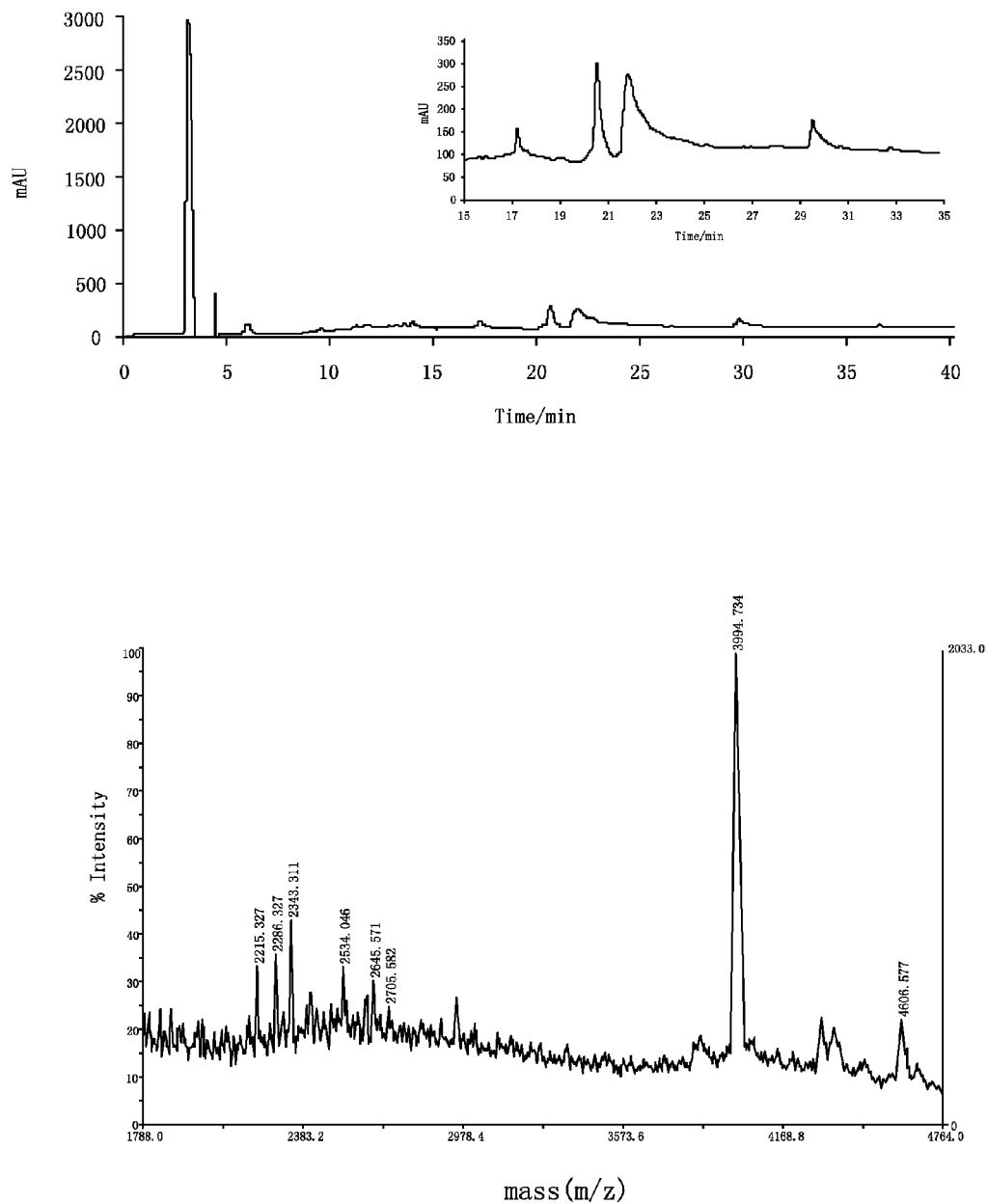
FIG. 5 shows the spectrum of a high performance liquid chromatography separation of folding reactions of chlorotoxin in different conditions in accordance with a fifth preferred embodiment of this disclosure.
Figure 6:
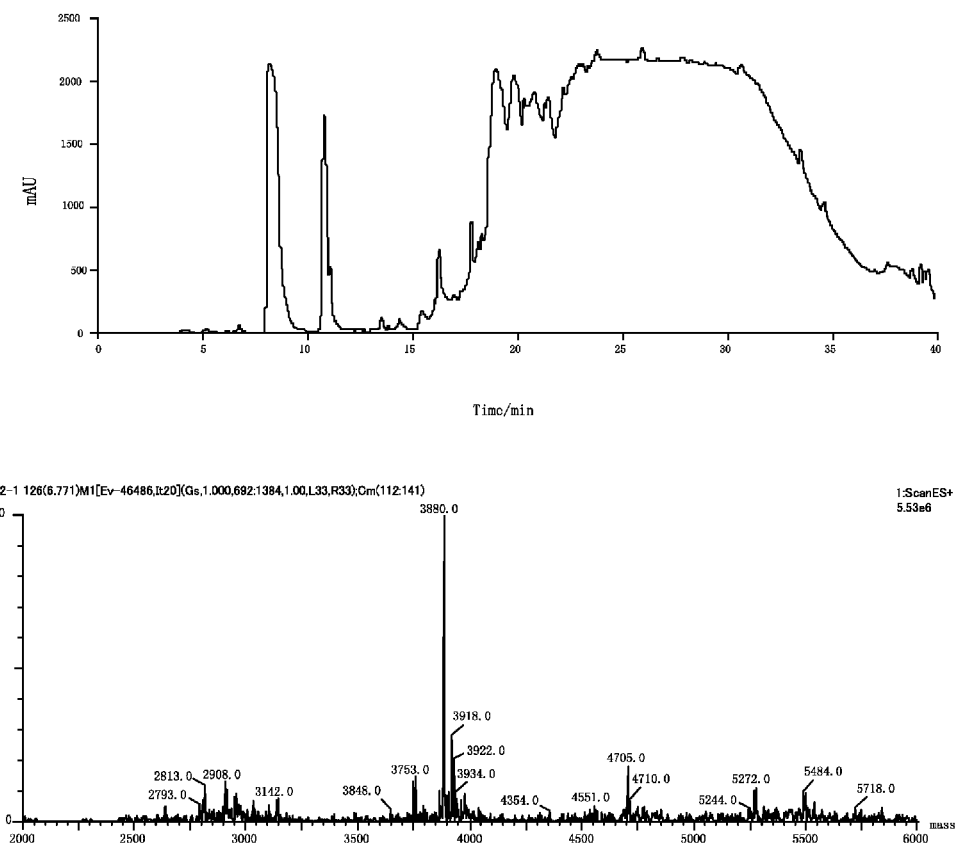
FIG. 6 shows the identification of a chlorotoxin variant by solid-state synthesis high performance liquid chromatography separation and liquid chromatography in accordance with a sixth preferred embodiment of this disclosure.
Figure 7:
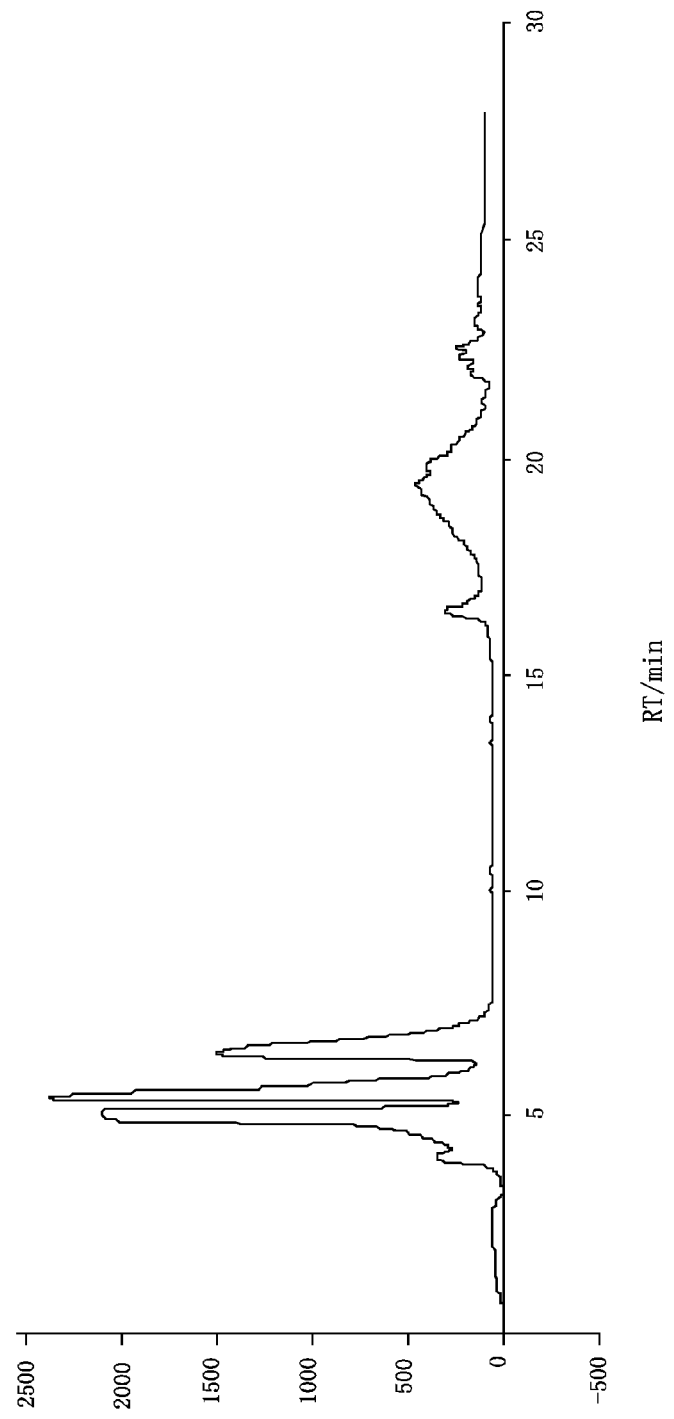
FIG. 7 shows the spectrum of a high performance liquid chromatography separation of the folding reaction of a chlorotoxin variant in different conditions in accordance with a seventh preferred embodiment of this disclosure.
Figure 8:
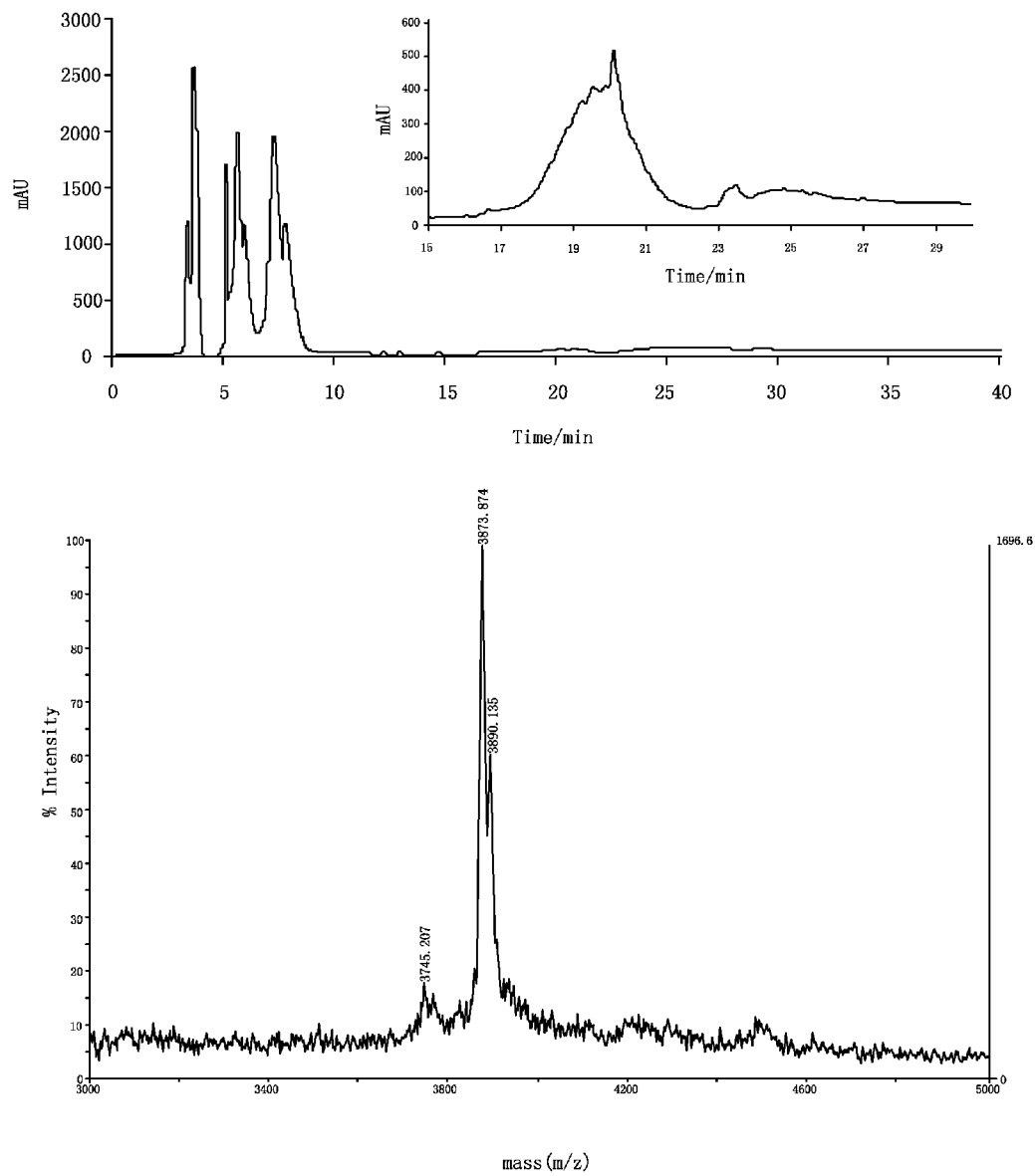
FIG. 8 shows the spectrum of high performance liquid chromatography separation and the mass spectrum of a chlorotoxin variant in accordance with an eighth preferred embodiment of this disclosure.

Weigh chlorotoxin (40 mg) and put it in a test tube containing a mixed solution of 100 Mmol bicarbonate, 2 Mmol guanidine hydrochloride, 10 Mmol glutathione, and 10% dimethylsulfoxide. Vortex the solution in the test tube for at least three times until the solution becomes transparent and clear. Set the system in a refrigerating chamber at 4 degrees C. for various time periods (1 hour, 2 hours, 4 hours, 6 hours, 10 hours, and 24 hours), and then remove the product. In the high performance liquid chromatography, Dionex C18 Acclaim 120 analytical column is used as the chromatographic column, and the velocity of flow is 1.00 ml/min, and the eluting phase includes 0.1% aqueous solution of trifluoroacetate, 0.1% trifluoroacetic acid in acetonitrile solution, and 5~65% gradient elution for 30 minutes, so as to obtain a separation spectrogram of the folded chlorotoxin.

Embodiment 2

Weigh chlorotoxin (40 mg) and put it in a test tube containing a mixed solution of 100 Mmol bicarbonate, 4 Mmol guanidine hydrochloride, 10 Mmol glutathione, and 10% dimethylsulfoxide. Vortex the solution in the test tube for at least three times until the solution becomes transparent and clear. Set the system in a refrigerating chamber at 4 degrees C. for various time periods (3 hours, 7 hours, and 24 hours), and then remove the product. In the high performance liquid chromatography, Dionex C18 Acclaim 120 analytical column is used as the chromatographic column, and the velocity of flow is 1.00 ml/min, and the eluting phase includes 0.1% aqueous solution of trifluoroacetate, 0.1% trifluoroacetic acid in acetonitrile solution, and 5~65% gradient elution for 30 minutes, so as to obtain a separation spectrogram of the folded chlorotoxin.

Embodiment 3

Weigh chlorotoxin (40 mg) and put it in a test tube containing a mixed solution of 100 Mmol bicarbonate, 2 Mmol guanidine hydrochloride, 100 Mmol glutathione, 10% dimethylsulfoxide. Vortex the solution in the test tube for at least three times until the solution becomes transparent and clear. Set the system in a refrigerating chamber at 4 degrees C. for various time periods (3 hours, 7 hours, and 24 hours), and then remove the product. In the high performance liquid chromatography, Dionex C18 Acclaim 120 analytical column is used as the chromatographic column, and the velocity of flow is 1.00 ml/min, and the eluting phase includes 0.1% aqueous solution of trifluoroacetate, 0.1% trifluoroacetic acid in acetonitrile solution, and 5~65% gradient elution 30 for minutes, so as to obtain a separation spectrogram of the folded chlorotoxin.

Embodiment 4

Weigh chlorotoxin (40 mg) and put it in a test tube containing a mixed solution of 100 Mmol bicarbonate, 2 Mmol guanidine hydrochloride, 200 Mmol glutathione, and 10% dimethylsulfoxide. Vortex the solution in the test tube for at least three times until the solution becomes transparent and clear. Set the system in a refrigerating chamber at 4 degrees C. for various time periods (3 hours and 7 hours), and then remove the product. In the high performance liquid chromatography, Dionex C18 Acclaim 120 analytical column is used as the chromatographic column, and the velocity of flow is 1.00 ml/min, and the eluting phase includes 0.1% aqueous solution of trifluoroacetate, 0.1% trifluoroacetic acid in acetonitrile solution, and 5~65% gradient elution for 30 minutes, so as to obtain a separation spectrogram of the folded chlorotoxin.

Embodiment 5

Weigh chlorotoxin and put it in a test tube containing a mixed solution of 100 Mmol bicarbonate, 2 Mmol disodium edetate, 3 Mmol reduced glutathione, and 1 Mmol oxidized glutathione and having a pH=7.8 (wherein the concentration of chlorotoxin is 0.05 mg/ml). Vortex the solution in the test tube for at least three times until the solution becomes transparent and clear. Set the system in a refrigerating chamber at 4 degrees C. for 6 days, and then remove the product. In the high performance liquid chromatography, Dionex C18 Acclaim 120 analytical column is used as the chromatographic column, and the velocity of flow is 1.00 ml/min, and the eluting phase includes 0.1% aqueous solution of trifluoroacetate, 0.1% trifluoroacetic acid in acetonitrile solution, and 5~65% gradient elution for 30 minutes, so that purified folded chlorotoxin is separated and obtained, wherein the retention time is 22.8 minutes, and the yield rate is 8%. The folded chlorotoxin and the four groups of bisulfide bonds so formed can pass the Moldi-TOF mass spectrometry split peak identification.

Embodiment 6

Weigh the amino acids according to the proportion in the sequence (MCMPCFTTDHQMARSCDDCCGGSGRG- SCYGPQCLCR-NH₂), and put them in a filler tube of a solid-state synthesizer. Weigh 3~10 times of resin and put it in a reactor. Turn on the solid-state synthesis of polypeptide, and let the reaction stop after 24~36 hours. The rough product is transferred, filtered, eluted, deprotected, rinsed with ice-cold ether, centrifuged, and vacuum freeze-dried. The rough product is injected in the high performance liquid chromatography, and Vydac C18 semi-preparative column is used for separation, and the velocity of flow is 3.00 ml/min, and the eluting phase includes 0.1% aqueous solution of trifluoroacetate, 0.1% trifluoroacetic acid in acetonitrile solution, and 5~65% gradient elution for 30 minutes, and the purified chlorotoxin variant is separated and obtained, wherein the retention time is 19.8 minutes, and the yield rate is 12%. The chlorotoxin variant can pass the split peak identification of LC-ESI liquid chromatography-mass spectrometry.

Embodiment 7

Weigh the chlorotoxin variant (38 mg) and put it in a test tube containing a mixed solution of 100 Mmol bicarbonate, 2 Mmol guanidine hydrochloride, 200 Mmol glutathione, and 10% dimethylsulfoxide. Vortex the solution in the test tube for at least three times until the solution becomes transparent and clear. Set the system in refrigerating chamber at 4 degrees C. for 24 hours and then remove the product. In the high performance liquid chromatography, Dionex C18 Acclaim 120 analytical column is used as the chromatographic column, and the velocity of flow is 1.00 ml/min, and the eluting phase includes 0.1% aqueous solution of trifluoroacetate, 0.1% trifluoroacetic acid in acetonitrile solution, and 5~65% gradient elution for 30 minutes, so as to obtain a separation spectrogram of the folded chlorotoxin.

Embodiment 8

Weigh chlorotoxin variant and put it in a test tube containing a mixed solution of 100 Mmol bicarbonate, 2 Mmol disodium edetate, 3 Mmol reduced glutathione, 1 Mmol oxidized glutathione and having a pH=7.8 (wherein the concentration of chlorotoxin variant is 0.05 mg/ml). Vortex the solution in the test tube for at least three times until the solution becomes transparent and clear. Set the system in a refrigerating chamber at 4 degrees C. for 6 days, and then remove the product. In the high performance liquid chromatography, Dionex C18 Acclaim 120 analytical column is used as the chromatographic column, and the velocity of flow is 1.00 ml/min, and the eluting phase includes 0.1% aqueous solution of trifluoroacetate, 0.1% trifluoroacetic acid in acetonitrile solution, and 5~65% gradient elution for 30 minutes, and the purified folded chlorotoxin variant is separated and obtained, wherein the retention time is 23.5 minutes, and the yield rate is 7%. The folded chlorotoxin variant and the four groups of bisulfide bonds so formed can pass the Moldi-TOF mass spectrometry split peak identification.

What is claimed is:

1. A preparation technology of a folded chlorotoxin with a peptide sequence of MCMPCFTTDHQMARKCDDCCG-GKGRGKCYGPQCLCR-NH$_2$ and a structural formula of:

comprising the steps of:

creating a reacting system according to the following proportion of numeric values by weighing 40 mg of chlorotoxin, and putting the chlorotoxin in a container containing a mixed solution of 100 Mmol bicarbonate, 2~4 Mmol guanidine hydrochloride, 10~200 Mmol glutathione, and 10 wt % dimethylsulfoxide; and vortexing the reacting system until the solution becomes transparent and clear, and setting the reacting system in a refrigerating chamber at 4 degrees C. for a reaction of 1~24 hours to obtain a folded chlorotoxin product.

2. A preparation technology of a folded chlorotoxin with a peptide sequence of MCMPCFTTDHQMARKCDDCCG-GKGRGKCYGPQCLCR-NH$_2$ and a structural formula of:

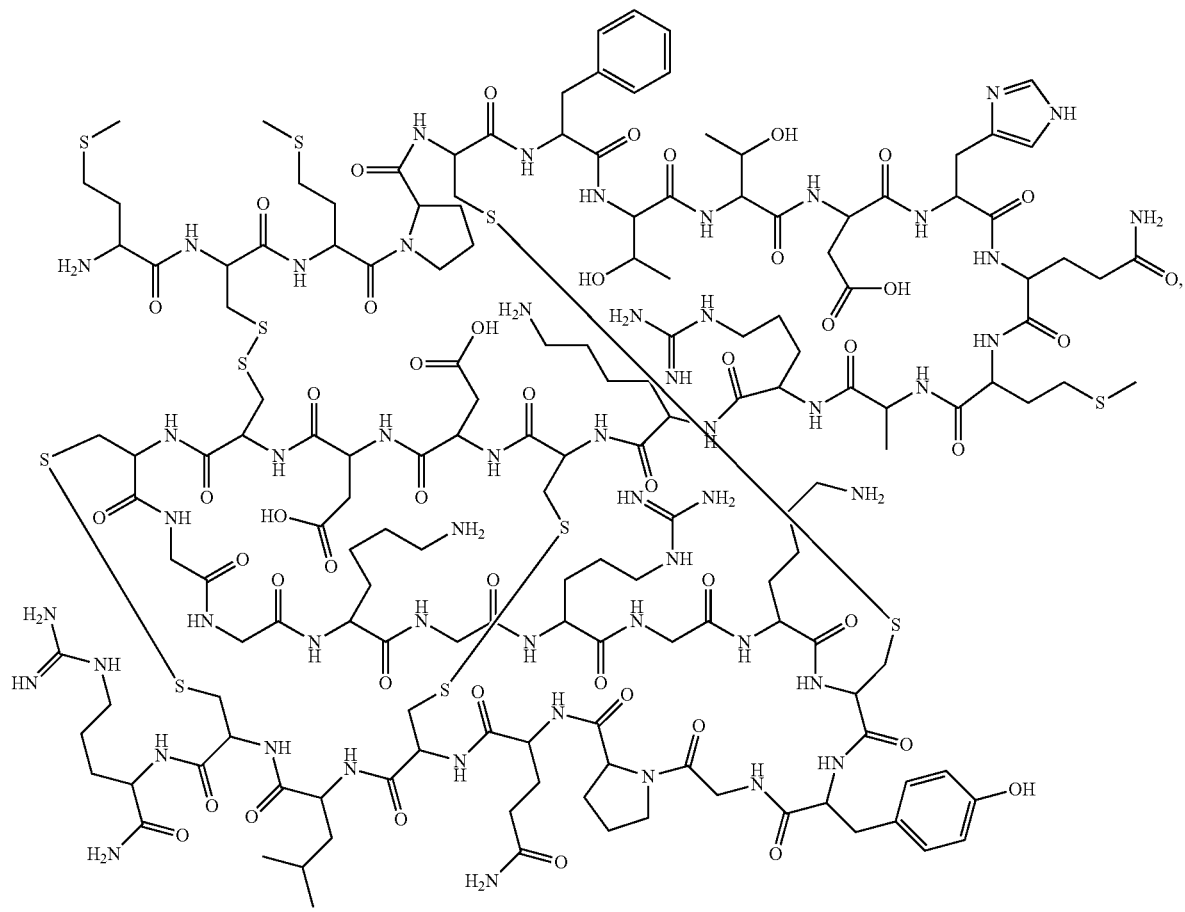 [SMILES: CSCCC(N)C(=O)NC1CSSCC2NC(=O)C(CC(=O)O)NC(=O)C(CC(=O)O)NC(=O)C3CSSCC4NC(=O)C(CCC(N)=O)NC(=O)C5CCCN5C(=O)CNC(=O)C(Cc5ccc(O)cc5)NC(=O)C(CSSCC(NC(=O)C5CCCN5C(=O)C(CCSC)NC1=O)C(=O)NC(Cc1ccccc1)C(=O)NC(C(C)O)C(=O)NC(C(C)O)C(=O)NC(CC(=O)O)C(=O)NC(Cc1c[nH]cn1)C(=O)NC(CCC(N)=O)C(=O)NC(CCSC)C(=O)NC(C)C(=O)NC(CCCNC(=N)N)C(=O)NC(CCCCN)C(=O)N3)NC(=O)C(CCCCN)NC(=O)CNC(=O)C(CCCNC(=N)N)NC(=O)CNC(=O)C(CCCCN)NC(=O)CNC(=O)CNC(=O)C(CSSCC(C(=O)NC(CCCNC(=N)N)C(N)=O)NC(=O)C(CC(C)C)NC4=O)NC2=O]
comprising the steps of:

creating a reacting system according to the following proportion of numeric values by weighing the chlorotoxin and putting the chlorotoxin in a container containing a mixed solution of 100 Mmol bicarbonate, 2 Mmol disodium edetate, 3 Mmol reduced glutathione, 1 Mmol oxidized glutathione and having a pH~7.8, wherein the reacting system has a chlorotoxin concentration of 0.05 mg/ml; and vortexing the reacting system until the solution becomes transparent and clear, and setting the reacting system in a refrigerating chamber at 4 degrees C. for a reaction of 6 days to obtain a folded chlorotoxin product.

* * * * *